(12) United States Patent
Lu et al.

(10) Patent No.: US 6,852,249 B2
(45) Date of Patent: Feb. 8, 2005

(54) PRISMATIC SUPRAMOLECULES

(75) Inventors: Kuang-Lieh Lu, Taipei (TW);
Manimaran Bala, Tamil Nadu (IN);
Thangamuthu Rajendran, Tamil Nadu (IN); Gene-Hsiang Lee, Taipei (TW);
Shie-Ming Peng, Taipei (TW);
Rong-Tang Liao, Taichung (TW);
Pounraj Thanasekaran, Tamil Nadu (IN)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/056,269

(22) Filed: Jan. 24, 2002

(65) Prior Publication Data

US 2003/0166920 A1 Sep. 4, 2003

(51) Int. Cl.[7] .......................... C07F 13/00; C07F 11/00; C07F 15/02; C09K 11/06
(52) U.S. Cl. ...................... 252/301.16; 546/2; 540/145; 544/179
(58) Field of Search ........................ 546/2; 252/301.16; 544/179; 540/145

(56) References Cited

U.S. PATENT DOCUMENTS

2003/0171582 A1 * 9/2003 Lu et al. ........................ 546/2
2004/0138455 A1 * 7/2004 Stossel et al. .................. 546/2

OTHER PUBLICATIONS

Dixon et al, Inorg. Chem., 39 (16), 3432–3433, 2000.*
Loudon, "Organic Chemistry, 3rd edition" (Benjamin/Cummings Publishing Co., 1995) pp. 271, 344.*
Stang et al., J. Am. Chem. Soc. 1997, vol. 119, 5163.*
Stang et al., Organometallics (1997) 16, 3094.*
Olenyuk et al., Nature, vol. 398 (1999), 796–799.*
Roche et al, Chem. Commun., 1998, 1681.*
Stephen M. Woessner, et al. *Self–Assembly of Ligand–Bridged Molecular Rectangles Containing fac–Re(CO)$_3$ Corners.* Inorganic Chemistry, vol. 37, No. 21, Oct. 19, 1998.
Shih–Sheng Sun, et al. *Self–Assembly Triangular and Square Rhenium(I) Tricarbonyl Complexes: A Comprehensive Study of Their Preparation, Electrochemistry, Photophysics, Photochemistry, and Host–Guest Properties.* J. Am. Chem. Soc., vol. 122, pp. 8956–8967, 2000.
Bala Manimaran, et al. *Self–Assembly of Fourteen Components into a Soluable, Neutral, Metalloprismatic Cage.* Eur. J. Inorg. Chem, 2001, pp. 633–636.
Bala Manimaran, etal. *Novel one–pot synthesis of luminescent neutral rhenium–based molecular rectangles.* J. Chem. Soc., Dalton Trans., 2001, pp. 515–517.

* cited by examiner

Primary Examiner—Mark L. Berch
(74) Attorney, Agent, or Firm—Fish & Richardson P.C.

(57) ABSTRACT

This invention features a supramolecule having the following structures:

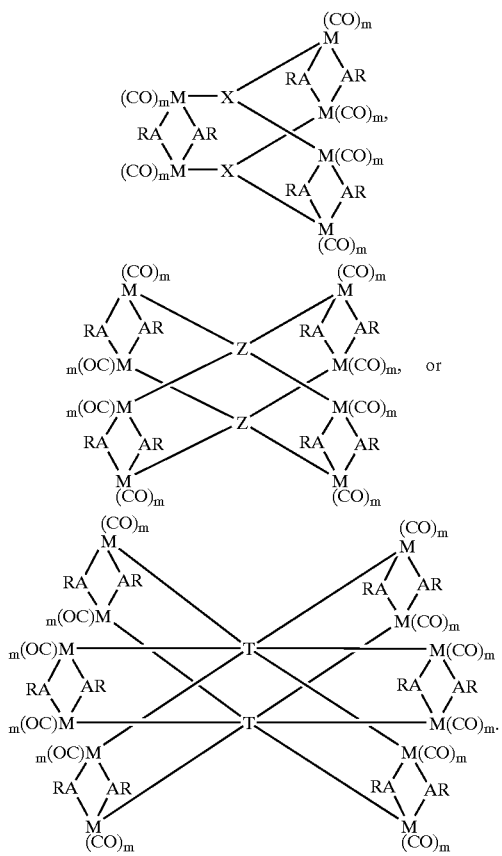

M is a transition metal atom that is rhenium (Re), manganese (Mn), chromium (Cr), molybdenum (Mo), tungsten (W), iron (Fe), ruthenium (Ru), or osmium (Os); X is a nitrogen-based tridentate ligand; Z is a nitrogen-based tetradentate ligand; T is a nitrogen-based hexadentate ligand; A is O, S, Se, or Te; R is $C_1$~$C_{16}$ alkyl, $(CH_2)_n$-aryl, or $(CH_2)_n$-aryl-(O—$C_1$~$C_{16}$ alkyl)$_p$, in which n is 0–15, p is 1–3; and m is 1, 2, 3, 4, or 5.

21 Claims, No Drawings

PRISMATIC SUPRAMOLECULES

BACKGROUND

Transition-metal-based supramolecules have been extensively explored in recent years. These supramolecules, which can be squares, helices, boxes, cages, or rectangles, are of particular interest due to their applications in host-guest interactions, molecular recognition, and as molecular sensors. See, e.g., Lehn, *Supramolecular Chemistry: Concepts and Perspectives*; VCH: Weinheim, 1995; Leininger, et al. (2000) *Chem. Rev.* 100: 853; Swiegers & Malefetse (2000) *Chem. Rev.* 100: 3483; Caulder & Raymond (1999) *J. Chem. Soc., Dalton Trans.* 1185; MacGillivray & Atwood (1999). *Angew. Chem. Int. Ed.* 38: 1018; Constable & Schofield (1998) *Chem. Commun.* 403; Fujita (1999) *Acc. Chem. Res.* 32: 53; Fujita (1998) *Chem. Soc. Rev.* 27: 417; Imamura & Fukushima (2000) *Coord. Chem. Rev.* 198: 133; Dixon et al. (2000) *Inorg. Chem.* 39: 3432; and Sun & Lees (2000) *J. Am. Chem. Soc.* 122: 8956.

It has been established that a transition-metal-based supramolecule offers the feasibility of host-guest interactions and molecular recognition phenomena based on Coulombic or hydrophobic binding, where the binding affinity is highly dependent on the cavity size inside the supramolecule (Sun & Lee supra). The cavity may function as a catalytic microreactor. The supramolecule has been known to possess a net charge and require a counterion within its cavity. The counterion affects the cavity size as well as molecular sensing properties of the supramolecule. It is desirable to design and prepare a supramolecule that is neutral.

In addition, incorporation of photo-active centers into a transition-metal-based supramolecule is also desirable in molecular sensing technology. This application provides an alternative to the detection of guest inclusion based on photoluminescence characteristics. For example, if a supramolecule is luminescent, it can be used as a tool in lieu of $^1$H NMR spectroscopy for detecting guest inclusion and studying electronic excited state reactivity and possible manipulation of reactivity by encapsulated guests. See, e.g., Slone et al. (1998) *Coord. Chem. Rev.* 171: 221; De Silva et al. (1997) *Chem. Rev.* 97: 1515; and Keefe et al. (2000) *Coord. Chem. Rev.* 205: 201.

There is a need for designing and preparing a transition-metal-based supramolecule that is neutral and luminescent.

SUMMARY

The invention is based on the discovery of four new classes of supramolecules having prismatic and rectangular structures. The new supramolecules are neutral and luminescent, and can be prepared by a one-pot synthesis method.

In one aspect, this invention features a prismatic supramolecule having structure (I):

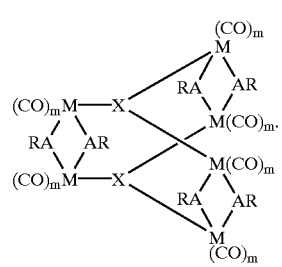

(I)

M is a transition metal atom that is rhenium (Re), manganese (Mn), chromium (Cr), molybdenum (Mo), tungsten (W), iron (Fe), ruthenium (Ru), or osmium (Os); X is a nitrogen-based tridentate ligand; A is O, S, Se, or Te; R is $C_1$–$C_{16}$ alkyl, $(CH_2)_n$-aryl, or $(CH_2)_n$-aryl-$(O$—$C_1$–$C_{16}$ alkyl$)_p$, in which n is 0–15, p is 1–3; and m is 1, 2, 3, 4, or 5. Other transition metal atoms may be utilized in accordance with the present invention as long as they, together with ligands, can form a coordination complex having the prismatic structures.

As used herein, the term "prismatic" refers to a compound having six transition metal atoms connected in a prismatic cage-like geometry. Each of the metal atoms occupies one corner of the prism and is bonded to one nitrogen of a nitrogen-based tridentate ligand, i.e., X in structure (I).

A "nitrogen-based tridentate ligand" refers to a ligand that is bonded to three transition metal atoms, and includes one or more heterocyclic or heteroaryl groups (e.g., triazine, pyrazole, imidazole, or pyridine) having one or more nitrogen atoms.

Referring to structure (I), a subset of prismatic supramolecules of this invention are those in which M is Re; m is 3; R is $C_1$–$C_{16}$ straight chain alkyl; A is O; and X is triazine or a ligand of the formula:

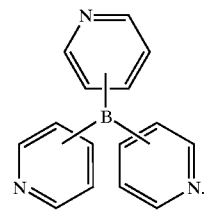

In the above formula, B is alkyl, alkenyl, alkynyl, cyclyl, heterocyclyl, aryl, or heteroaryl (e.g., 1,3,5-triazine); further, the three rings can be fused together with B (not shown), e.g., triaza-triphenylene or triaza-trinaphthylene. An example of X is 2,4,6-tri-4-pyridyl-1,3,5-triazine (referred to hereinafter as "tpt").

Additional examples of X are shown below:

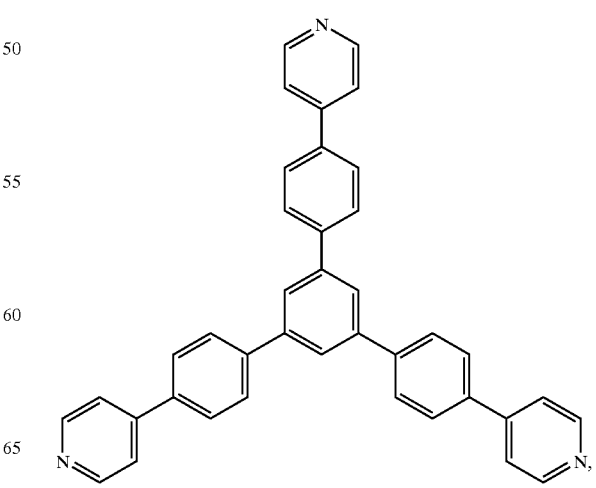

-continued

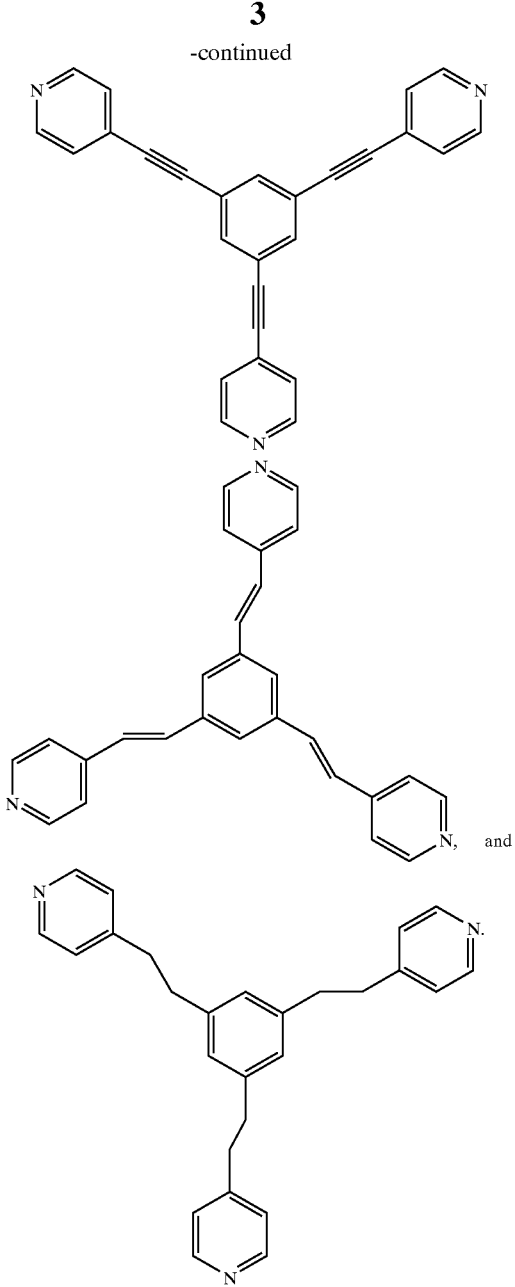

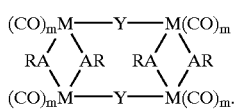

In another aspect, this invention features a rectangular supramolecule having structure (II):

$$(CO)_mM\text{---}Y\text{---}M(CO)_m$$
$$RA\phantom{--}AR\phantom{--}RA\phantom{--}AR$$
$$(CO)_mM\text{---}Y\text{---}M(CO)_m.$$

M is a transition metal atom that is Re, Mn, Cr, Mo, W, Fe, Ru, or Os; Y is a nitrogen-based didentate ligand; A is O, S, Se, or Te; R is $C_3$~$C_{16}$ alkyl, $(CH_2)_n$-aryl, or $(CH_2)_n$-aryl-(O—$C_1$~$C_{16}$ alkyl)$_p$, in which n is 0–15, p is 1–3; and m is 1, 2, 3, 4, or 5.

As used herein, the term "rectangular" refers to a compound having four transition metal atoms connected in a rectangular geometry. Each of the transition metal atoms occupies one corner of the rectangle, and is bonded to one nitrogen atom of a nitrogen-based didentate ligand.

A "nitrogen-based didentate ligand" refers to a ligand that is bonded to two transition metal atoms, and includes one or more heterocyclic or heteroaryl groups having one or more nitrogen atoms.

Referring to structure (II), a subset of rectangular supramolecules of this invention are those in which M is Re; m can be 3; R is $C_3$~$C_{16}$ straight chain alkyl; A is O; and Y is diazine or a ligand of the formula:

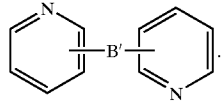

B' is a bond, alkyl, alkenyl, alkynyl, cyclyl, heterocyclyl, aryl, or heteroaryl; further, the two rings can be fused together with B (not shown), e.g., diaza-anthracene or 1,6-Dihydro-benzo[lmn][3,8]phenanthroline. Examples of Y include

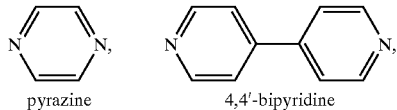

pyrazine      4,4'-bipyridine

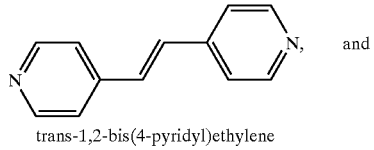

trans-1,2-bis(4-pyridyl)ethylene

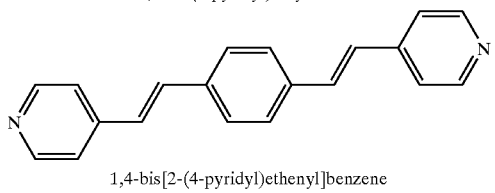

1,4-bis[2-(4-pyridyl)ethenyl]benzene (referred to hereinafter as "pz," "bpy," "bpe," or "bpeb," respectively).

Additional examples of Y are shown below:

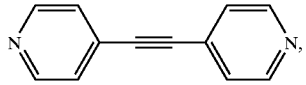

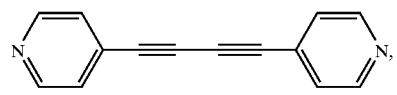

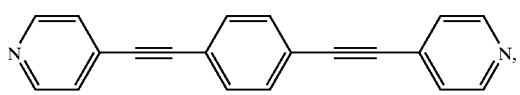

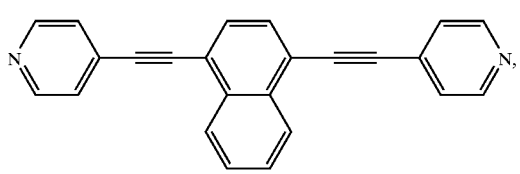

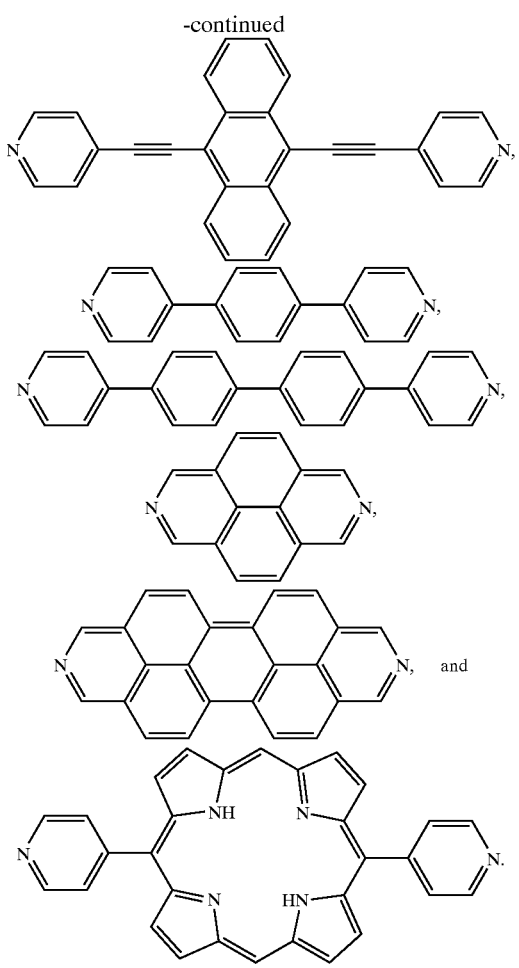

In further another aspect, this invention features a tetragonal prismatic supramolecule having structure (III):

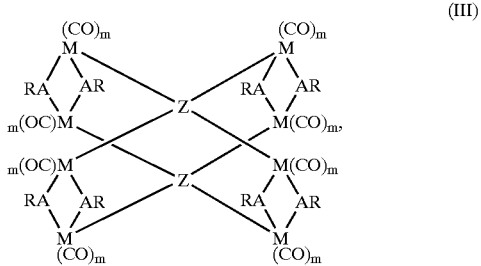

(III)

M is Re, Mn, Cr, Mo, W, Fe, Ru, or Os; Z is a nitrogen-based tetradentate ligand; A is O, S, Se, or Te; R is $C_1$–$C_{16}$ alkyl, $(CH_2)_n$-aryl, or $(CH_2)_n$-aryl-$(O-C_1-C_{16}$ alkyl$)_p$, in which n is 0–15, p is 1–3; and m is 1, 2, 3, 4, or 5.

As used herein, the term "tetragonal prismatic" refers to a compound having eight transition metal atoms connected in a prismatic cage-like geometry. Each of the metal atoms occupies one corner of the prism and is bonded to one nitrogen of a nitrogen-based tetradentate ligand, i.e., Z in structure (III).

A "nitrogen-based tetradentate ligand" refers to a ligand that is bonded to four transition metal atoms, and includes one or more heterocyclic or heteroaryl groups (e.g., triazine, pyrazole, imidazole, or pyridine) having one or more nitrogen atoms.

Referring to structure (III), a subset of tetragonal prismatic supramolecules of this invention are those in which M is Re; m is 3; R is $C_1$–$C_{16}$ straight chain alkyl; A is O; and Z is tetrazine or a ligand of the formula:

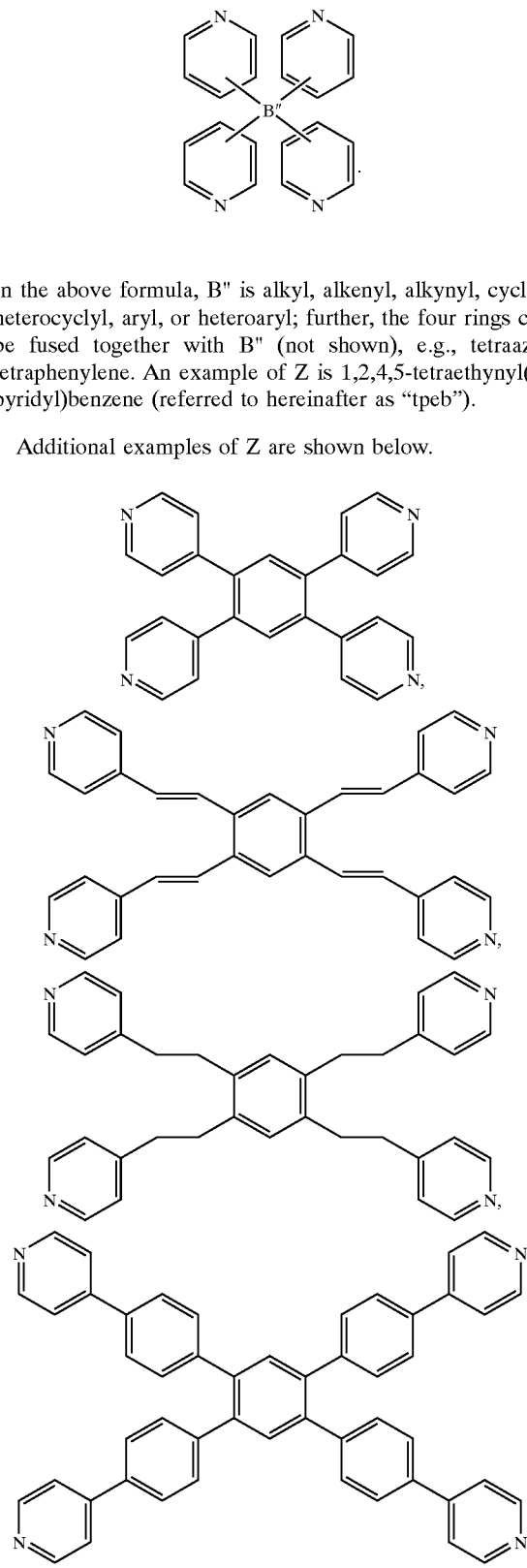

In the above formula, B" is alkyl, alkenyl, alkynyl, cyclyl, heterocyclyl, aryl, or heteroaryl; further, the four rings can be fused together with B" (not shown), e.g., tetraaza-tetraphenylene. An example of Z is 1,2,4,5-tetraethynyl(4-pyridyl)benzene (referred to hereinafter as "tpeb").

Additional examples of Z are shown below.

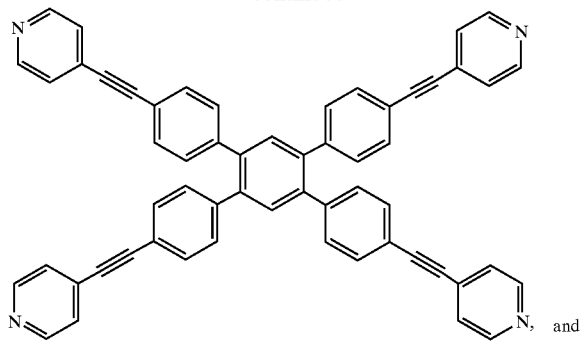

and

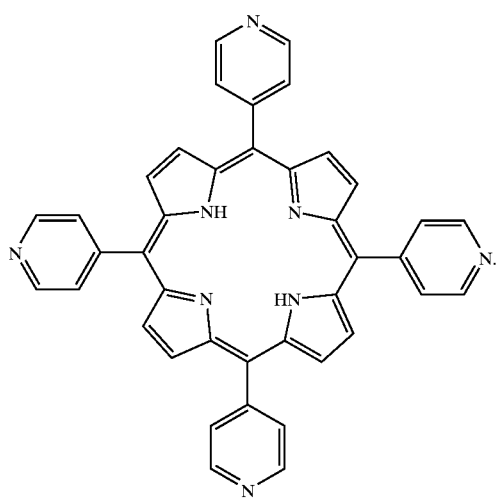

In still another aspect, this invention features a hexagonal prismatic supramolecule having structure (IV):

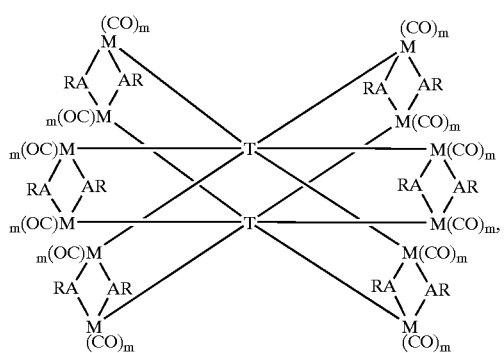

(IV)

M is Re, Mn, Cr, Mo, W, Fe, Ru, or Os; T is a nitrogen-based hexadentate ligand; A is O, S, Se, or Te; R is $C_1$~$C_{16}$ alkyl, $(CH_2)_n$-aryl, or $(CH_2)_n$-aryl-$(O$—$C_1$~$C_{16}$ alkyl$)_p$, in which n is 0–15, p is 1–3; and m is 1, 2, 3, 4, or 5.

As used herein, the term "hexagonal prismatic" refers to a compound having twelve transition metal atoms connected in a prismatic cage-like geometry. Each of the metal atoms occupies one corner of the prism and is bonded to one nitrogen of a nitrogen-based hexadentate ligand, i.e., T in structure (IV).

A "nitrogen-based hexadentate ligand" refers to a ligand that is bonded to six transition metal atoms, and includes one or more heterocyclic or heteroaryl groups (e.g., triazine, pyrazole, imidazole, or pyridine) having one or more nitrogen atoms.

Referring to structure (IV), a subset of hexagonal prismatic supramolecules of this invention are those in which M is Re; m is 3; R is $C_1$~$C_{16}$ straight chain alkyl; and A is O.

Examples of T are shown below.

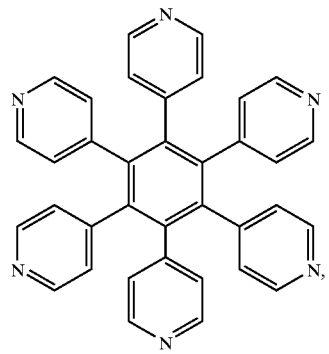

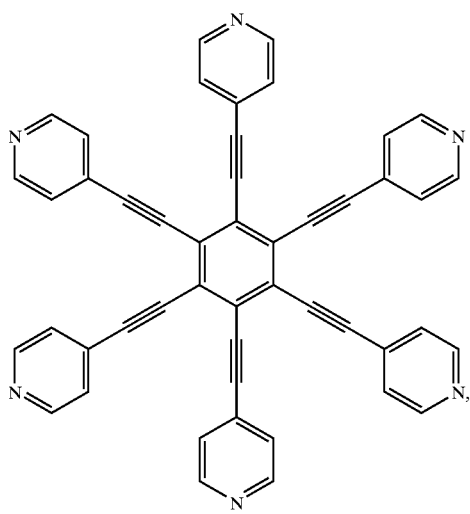

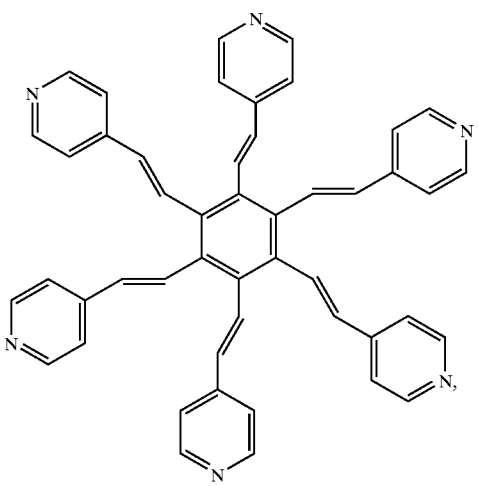

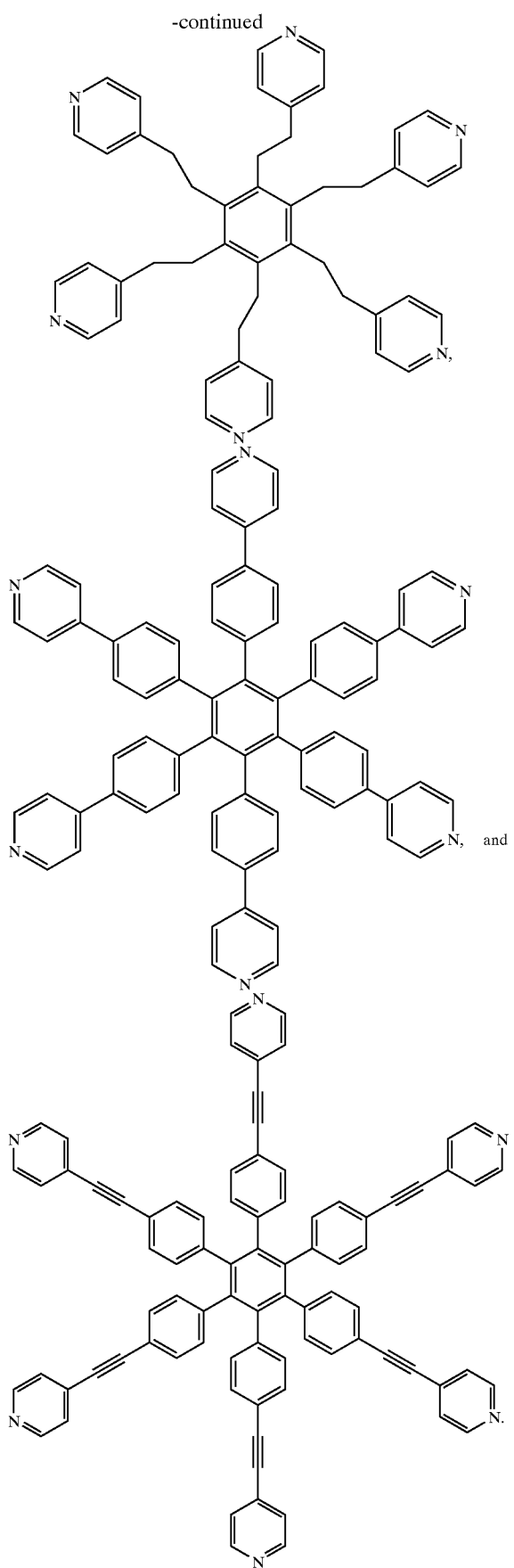

Alkyl, alkenyl, alkynyl, cyclyl, heterocyclyl, aryl, or heteroaryl (e.g., triazine, diazine, or pyridine) mentioned above include both substituted and unsubstituted moieties. As used herein, alkyl, alkenyl, alkynyl are straight or branched hydrocarbon chains. The term "substituted" refers to one or more substituents (which may be the same or different), each in replace of a hydrogen atom. Examples of substituents include, but are not limited to, halogen, hydroxyl, amino, cyano, nitro, $C_1\sim C_6$ alkyl, $C_2\sim C_6$ alkenyl, $C_2\sim C_6$ alkynyl, $C_1\sim C_6$ alkoxy, aryl, heteroaryl, and heterocyclyl, wherein alkyl, alkenyl, alkoxy, aryl, heteroaryl and heterocyclyl are optionally substituted with $C_1\sim C_6$ alkyl, $C_2\sim C_6$ alkenyl, $C_2\sim C_6$ alkynyl, aryl, heteroaryl, halogen, hydroxyl, amino, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, pyridyl, carbazolyl, and indolyl.

Set forth below are exemplary compounds of this invention:

Compounds 1–3 having prismatic structure (I), in which M is Re; m is 3; and A is O;

Compound 1: $R=C_4H_9$; X=tpt;

Compound 2: $R=C_8H_{17}$; X=tpt; and

Compound 3: $R=C_{12}H_{25}$; X=tpt;

Compounds 4–12 having rectangular structure (II), in which M is Re; m is 3; and A is O;

Compound 4: $R=(CH_2)_3CH_3$; Y=pz;

Compound 5: $R=(CH_2)_7CH_3$; Y=pz;

Compound 6: $R=(CH_2)_3CH_3$; Y=bpe;

Compound 7: $R=(CH_2)_7CH_3$; Y=bpe;

Compound 8: $R=(CH_2)_3CH_3$; Y=bpeb;

Compound 9: $R=(CH_2)_3CH_3$; Y=pz;

Compound 10: $R=(CH_2)_3CH_3$; Y=bpy;

Compound 11: $R=(CH_2)_7CH_3$; Y=bpy; and

Compound 12: $R=(CH_2)_{11}CH_3$; Y=bpy.

Compounds 13–15 having tetragonal prismatic structure (III), in which M is Re; m is 3; and A is O;

Compound 13: $R=C_8H_{17}$; Z=tpeb;

Compound 14: $R=C_{12}H_{25}$; X=tpeb; and

Compound 15: $R=C_7H_7$; X=tpeb.

In still another aspect, this invention features a one-pot synthesis method for making a prismatic supramolecule of this invention. The method includes reacting $M(CO)_{m+2}$ with a nitrogen-based tridentate ligand in the presence of an RAH (see structure (I), e.g., a $C_1\sim C_{16}$ aliphatic alcohol) at an elevated temperature to form a thermodynamically stable prismatic supramolecule. When RAH is an alcohol, the reaction can be carried out using a solvothermal approach or a refluxing approach. In the solvothermal approach, the alcohol serves as the only solvent and also as one reactant. In the refluxing approach, one or more other organic solvents can be used together with the alcohol.

In further another aspect, this invention features a one-pot synthesis method for making a rectangular supramolecule having structure (II):

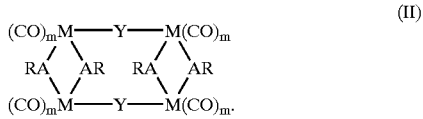

(II)

M is Re, Mn, Cr, Mo, W, Fe, Ru, or Os; Y is a nitrogen-based didentate ligand; A is O, S, Se, or Te; R is $C_1$~$C_{16}$ alkyl or $(CH_2)_n$-aryl, in which n is 0–15; and m is 1, 2, 3, 4, or 5. This method includes reacting $M(CO)_{m+2}$ with a nitrogen-based didentate ligand in the presence of an RAH at an elevated temperature to form the rectangular supramolecule.

Additionally, this invention features a one-pot synthesis method for making a tetragonal prismatic supramolecule of this invention. The method includes reacting $M(CO)_{m+2}$ with a nitrogen-based tetradentate ligand in the presence of an RAH (see structure (III), e.g., a $C_1$~$C_{16}$ aliphatic alcohol) at an elevated temperature to form a thermodynamically stable tetragonal prismatic supramolecule.

Further, this invention also feature a one-pot synthesis method for making a hexagonal prismatic supramolecule of this invention. The method includes reacting $M(CO)_{m+2}$ with a nitrogen-based hexadentate ligand in the presence of an RAH (see structure (IV), e.g., a $C_1$~$C_{16}$ aliphatic alcohol) at an elevated temperature to form a thermodynamically stable hexagonal prismatic supramolecule.

Also within the scope of this invention is a composition for emitting luminescence at room temperature. The composition can include an aqueous solution (e.g., a mixture of THF and $H_2O$, a mixture of $CH_3CN$ and $H_2O$, a mixture of $CH_3COCH_3$ and $H_2O$, a mixture of $CH_3OH$ and $H_2O$, or a mixture of $CH_3CH_2OH$ and $H_2O$) and a rectangular supramolecule having structure (II):

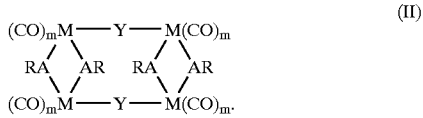

(II)

M is Re, Mn, Cr, Mo, W, Fe, Ru, or Os; Y is a nitrogen-containing didentate ligand; A is O, S, Se, or Te; R is $C_1$~$C_{16}$ alkyl or $(CH_2)_n$-aryl, in which n is 0–15; and m is 1, 2, 3, 4, or 5. Preferably, R is $C_8$~$C_{12}$ straight chain alkyl. Alternatively, the composition can include a prismatic supramolecule of this invention and an aqueous solution. Further, the composition can include a tetragonal prismatic supramolecule of this invention and a solution, such as pyridine, methyl phenyl sulfide, or an aqueous solution described above.

The invention provides several advantages. For example, the four new classes of supramolecules (i.e., having prismatic and rectangular structures) described above are neutral, air and moisture stable, and soluble in organic and polar solvents. In addition, the supramolecules exhibit luminescence.

Other advantages, features, and objects of the invention will be apparent from the description and from the claims.

DETAILED DESCRIPTION

The invention covers four new classes of supramolecules having prismatic and rectangular structures. Such supramolecules described in the "Summary" section can be prepared by methods also within the scope of this invention. More specifically, one can react $M(CO)_{m+2}$ (M is Re, Mn, Cr, Mo, W, Fe, Ru, or Os; and m is any single number between 1–5) with a nitrogen-based di-, tri-, tetra-, or hexa-dentate ligand in the presence of an RAH (see structures (I) (II), (III), and (IV) above, e.g., a $C_1$~$C_{16}$ aliphatic alcohol) at an elevated temperature to form a supramolecule. For example, when the RAH is an alcohol, the reaction can be carried out using a solvothermal approach, in which the alcohol serves as the only solvent and also as a reactant. In this approach, the reaction temperature is higher than the boiling point of the alcohol. The reaction proceeds until the most thermodynamically stable supramolecule forms. Unexpectedly, this reaction affords supramolecule crystals of high quality, such as X-ray quality crystals. If necessary, the supramolecule can be further purified by flash column chromatography, high performance liquid chromatography, or re-crystallization. One can design and prepare a supramolecule having desired structures and physical properties (e.g., prismatic cages, rectangles, cavity sizes, or hydrophobicities) by adjusting the experimental conditions and choosing an appropriate ligand.

The supramolecules described above are useful in molecular sensing technology. Many of the previously reported supramolecules are charged, with counterions trapped inside the cavities of the charged supramolecules. The trapped counterions interfere with host-guest interactions or affect molecular sensing properties. In contrast, the supramolecules of this invention are neutral and have no counterions inside their cavities. Additionally, such supramolecules can obtain various di-, tri-, tetra-, or hexa-dentate ligands and therefore, possess diverse size cavities, making them suitable as hosts for a variety of guest molecules in the solid state as well as in solution. Thus, the supramolecules in accordance with the present invention may be used to detect and measure the inclusion of guest molecules of varying sizes, including aromatic hydrocarbons (e.g., anthracene, p-xylene, pyrene, phenanthrene, triphenylene, chrysene, benzopyrene, dicyanobenzene, or benzanthracene), nitro compounds (e.g., nitrobenzene, m-dinitrobenzene, nitrotoluene, 2,4-dinitrotoluene, or 2,6-dinitrotoluene), amines (e.g., tetramethylphenylenediamine, tetramethylbenzidene, p-anisidene, or diphenylamine), quinines (e.g., toluiquinone, benzoquinone, naphthaquinone, or anthraquinone), and some metal salts (e.g., $AgNO_3$, $Zn(NO_3)_2$, $Co(NO_3)_2$, or $Cd(NO_3)_2$) or complexes (e.g., $[Ru(bpy)_3]Cl_2$).

The detection and measurement can be based on the supramolecules' electrochemical properties (e.g., showing changes in redox potential values), photophysical/photochemical properties (e.g., showing changes in emission or absorption spectra), or solvatochromism (e.g., showing visible color changes depending on the polarity of a solvent). The NMR technique is one conventional method for detecting and measuring host-guest interactions.

More specifically, the rectangular or prismatic supramolecules described above exhibit luminescence in a solution, and therefore are useful in molecular sensors for detecting and measuring the inclusion of target molecules based on photoluminescence characteristics. The exhibited luminescence of these supramolecules is unexpectedly bright when the supramolecules are in an aqueous solution. The brightness in an aqueous solution may be due to self-aggregation of the supramolecules, and can be used effectively in sensor applications. For example, the rectangular supramolecules in an aqueous solution provide a more sensitive spectroscopic detection technique than the conventional NMR method for monitoring host-guest interactions.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of Compounds 1–3 Having Prismatic Structures

A suspension consisting of a mixture of $Re_2(CO)_{10}$ (98 mg, 0.15 mmol) and tpt (32 mg, 0.10 mmol) in 10 mL 1-butanol in a 30 mL Teflon flask was placed in a steel bomb. The bomb was placed in an oven maintained at 180° C. for 48 h and then cooled to 25° C. Good quality maroon colored single crystals of Compound 1 were obtained. The crystals were separated by filtration and washed with 1-butanol. Compounds 2 and 3 were also synthesized by adopting a similar procedure. The solvent from the reaction mixture was removed by vacuum distillation and the residue was redissolved in $CH_2Cl_2$ and passed through short silica gel column to get the pure products of Compounds 2 and 3. (Yield: Compound 1, 109 mg, 81%; Compound 2, 124 mg, 82%; Compound 3, 142 mg, 85%)

$[\{(CO)_3Re(\mu_2\text{-}OC_4H_9)_2Re(CO)_3\}_3(\mu_3\text{-tpt})_2]$ (Compound 1): Elemental analysis: Calcd: C, 34.89; H, 2.93; N, 6.26; found: C, 35.06; H, 2.94; N, 6.40; Crystal data ($C_{78}H_{78}N_{12}O_{24}Re_6$): Crystal dimensions 0.20×0.10×0.03 mm, rhombohedral, space group R3̄c, a=b=23.4486(9), c=27.6604(11) Å, α=β=90, γ=120°, V=13171.1(9) Å$^3$, Z=6, T=150(1) K, $\rho_{calcd}$=2.031 Mg/m$^3$, $\mu$=8.316 mm$^{-1}$, 9628 total reflections, 2539 independent reflections which were used in refinement. The structure was solved to R1=0.0865 and wR2=0.1166.

$[\{(CO)_3Re(\mu_2\text{-}OC_8H_{17})_2Re(CO)_3\}_3(\mu_3\text{-tpt})_2]$ (Compound 2): IR ($CH_2Cl_2$); $\nu_{CO}$ 2022 (s), 2009 (m), 1913 (m), 1890 (vs) cm$^{-1}$; $^1$H NMR (300 MHz, CDCl$_3$): δ 8.72 (d, $^3$J=6.5 Hz, 12H, H$^3$), 8.24 (d, 12H, H$^2$), 4.43 (t, $^3$J=8.0 Hz, 12H), 2.15 (m, 12H), 1.49 (m, 36H), 1.25 (m, 24H), 0.94 (t, $^3$J=6.7 Hz, 18H); $^{13}$C NMR (75 MHz; CDCl$_3$): δ=197.2 (s, CO), 170.1 (C, triazine), 153.5 (C$^3$), 142.2 (C$^1$), 123.2 (C$^2$), 82.9 ($CH_2$), 34.2 ($CH_2$), 31.9 ($CH_2$), 29.7 ($CH_2$), 29.4 ($CH_2$), 25.3 ($CH_2$), 22.7 ($CH_2$), 14.2 ($CH_3$); UV-Vis ($CH_2Cl_2$): $\lambda_{max}$ [nm] (MLCT) 488, $\lambda_{max}$ [nm] (LIG) 243; Elemental analysis: Calcd: C, 40.55; H, 4.20; N, 5.56; found: C, 40.56; H, 4.23; N, 5.53; Mass (FAB, $^{187}$Re): m/z=3024 (M$^+$).

$[\{(CO)_3Re(\mu_2\text{-}OC_{12}H_{25})_2Re(CO)_3\}_3(\mu_3\text{-tpt})_2]$ (Compound 3): IR ($CH_2Cl_2$): $\nu_{CO}$ 2022 (s), 2009 (m), 1913 (m), 1890 (vs) cm$^{-1}$; $^1$H NMR (300 MHz, CDCl$_3$): δ=8.72 (d, $^3$J=6.5 Hz, 12H, H$^3$), 8.24 (d, 12H, H$^2$), 4.42 (t, $^3$J=8.0, 12H), 2.15 (m, 12H), 1.48 (m, 24H), 1.29 (m, 84H), 0.88 (t, $^3$J=6.2 Hz, 18H); $^{13}$C NMR (75 MHz; CDCl$_3$): δ=197.2, 197.1 (s, 1:2CO), 170.1 (C, triazine), 153.5 (C$^3$), 142.1 (C$^1$), 123.2 (C$^2$), 82.8 ($CH_2$), 34.1 ($CH_2$), 31.9 ($CH_2$), 31.5 ($CH_2$), 29.7 (2$CH_2$), 29.6 (2$CH_2$), 29.3 ($CH_2$), 25.2 ($CH_2$), 22.7 ($CH_2$), 14.1 ($CH_3$); UV-Vis ($CH_2Cl_2$): $\lambda_{max}$ [nm] (MLCT) 488, $\lambda_{max}$ [nm] (LIG) 242; Elemental analysis: Calcd: C, 44.99; H, 5.22; N, 5.00; found: C, 45.52; H, 5.30; N, 4.92; Mass (FAB, $^{187}$Re): m/z=3360 (M$^+$).

The ORTEP drawing of Compound 1 revealed a prismatic cage architecture, where two planar tpt ligands coordinated to six rhenium atoms, which were connected by six butoxo bridges, thereby forming a triangular prismatic cage. Each rhenium atom occupied the corner of the triangular prism and was bonded to one nitrogen atom of the pyridyl group of the tpt ligand, two butoxy groups and three carbonyl groups, maintaining a distorted octahedral geometry around it. The maximum and minimum rhenium-rhenium distances in the molecule were 13.5 and 3.4 Å respectively. The three pyridyl rings of tpt moiety were canted slightly ca. 15° from the plane containing the triazine ring. Some group of researchers have experienced difficulty to grow X-ray quality single crystals, in the case of metallomacromolecules containing more metal centers. See, e.g., Sun et al. (2000) *Inorg. Chem.* 39: 1344–1345; Sun & Lees (1999) *Inorg. Chem.* 38: 4181–4182; Constable & Schofield (1998) *Chem. Commun.* 403–404; and Manna, (1997) *J. Am. Chem. Soc.* 119: 11611–11619. In contrast, the synthetic strategy described above has led to the formation of single crystals of good quality. The electroneutrality of the cage Compounds 1–3 mitigated interference of the counter ions inside the cavity, which created problem in most of the sensor studies. The extraordinary affinity of oxygen with rhenium metal was emphasized in this synthetic approach by utilizing the oxo-bridges bearing hydrophobic long tails. The $^1$H and $^{13}$C NMR spectral measurements and the FAB-MS data of the cage compounds were in agreement with the proposed structures.

Interestingly the solubility of Compounds 1–3 has been improved enormously by changing the length of the alkyl moiety from butyl to octyl and then to dodecyl. The increase in the chain length of the alkoxo moiety increased the hydrophobicity of the cage, thereby increasing the solubility of the compound in organic solvents. Compounds 2 and 3 were freely soluble in $CH_2Cl_2$, $(CH_3)_2CO$ and other organic solvents compared to Compound 1. Because of the greater solubility of Compounds 2 and 3, the latter were used for further studies.

Compounds 2 and 3 displayed an identical CO stretching pattern in their infrared spectra which was similar to that observed for the previously reported compounds. See, e.g., Benkstein et al. (1988) *Inorg. Chem.* 37: 5404–5405; Jiang et al. (1998) *Organometallics* 17: 173–181; and El-Sayed & Kaesz (1963) *Inorg. Chem.* 2: 158–162. The UV-Vis spectra of Compounds 2 and 3 in $CH_2Cl_2$ showed an intense high energy band at 243 nm and a broad low-energy band at 488 nm, respectively. In accord with the previous reports on related systems, the former absorption was assigned to the intraligand π–π* transition and the low energy absorption to a metal-to-ligand charge transfer (MLCT) transition. In addition, there was a shoulder at about 265 nm, which may be assigned to another π–π* transition as suggested by Tapolsky et al. See, e.g., Tapolsky et al. (1991) *J. Phys. Chem.* 95: 1105–1112; Tapolsky et al. (1990) *Inorg Chem.* 29: 2285–2297; and Tapolsky et al. (1989) *J. Phys. Chem.* 93: 3885–3887. The interesting feature that deserved further attention was the observation of MLCT at comparatively large wavelength (488 nm), indicating the readily reducible nature of the ligand. The absorption spectra of Compounds 2 and 3 were recorded in a large number of solvents and they showed substantial solvatochromism; the $\lambda_{max}^{ab}$ value could be tuned over 125 nm with a change in the color of the solution from yellow to red with the change in polarity of the solvents ($\lambda_{max}^{ab}$ values for Compound 2 in DMSO and $CCl_4$ are 424 and 549 nm, respectively). See, e.g., Reichardt (1994) *Chem. Rev.* 94: 2319–2358.

EXAMPLE 2

Synthesis and Characterization of Compounds 4–9 Having Rectangular Structures

In a typical preparation, a suspension containing a mixture of $Re_2(CO)_{10}$ and the N-ligands in 10 ml aliphatic alcohol in a 30 ml Teflon flask was placed in an oven maintained at 120–160° C. and then cooled to 25° C. The crystals were separated by filtration and the solvent from the filtrate was removed by vacuum and the residue was redissolved in minimum quantity of $CH_2Cl_2$ and passed through a short silica gel column to get the pure product.

[{$(CO)_3Re(\mu$-$OC_4H_9)_2Re(CO)_3$}$_2(\mu$-pz)$_2$] (Compound 4): Yield: 71%. IR ($CH_2Cl_2$): $\nu_{CO}$ 2024 (s), 2017 (sh, m), 1925 (m), 1903 (vs) cm$^{-1}$; $^1$H NMR (300 MHz, $(CD_3)_2CO$): $\delta$ 8.83 (s, 8H, H$^2$), 4.44 (m, 8H), 2.17 (m, 8H), 1.48 (m, 8H), 1.07 (t, $^3J$=7.4 Hz, 12H); $^{13}$C NMR (75 MHz; $(CD_3)_2CO$): $\delta$=199.0, 198.2 (1:2, CO), 150.1 (C$^2$, pyrazine), 82.9 ($CH_2$), 36.5 ($CH_2$), 19.0 ($CH_2$), 14.5 ($CH_3$); UV-VIS ($CH_3CN$): $\lambda_{max}$ [nm] 452 (MLCT), 255, 261, 268 (LIG); Anal. for $C_{36}H_{44}N_4O_{16}Re_4$, Found (calcd): C, 28.09 (28.19); H, 2.85 (2.89); N, 3.73 (3.65); Mass (FAB, $^{187}$Re): m/z=1536 (M$^+$).

[{$(CO)_3Re(\mu$-$OC_8H_{17})_2Re(CO)_3$}$_2(\mu$-pz)$_2$] (Compound 5): Yield: 73%. IR ($CH_2Cl_2$): $\nu_{CO}$ 2024 (s), 2018 (sh, m), 1924 (m), 1903 (vs) cm$^{-1}$; $^1$H NMR (300 MHz, $(CD_3)_2$CO)): $\delta$ 8.83 (s, 8H, H$^2$), 4.42 (m, 8H), 2.20 (m, 8H), 1.46 (m, 24H), 1.35 (m, 16H). 0.91 (t, $^3J$=6.9 Hz, 12H); $^{13}$C NMR (75 MHz; $(CD_3)_2CO$): $\delta$=198.7, 197.1 (1:2, CO), 150.0 (C$^2$, pyrazine), 83.1 ($CH_2$), 34.2 ($CH_2$), 32.5 ($CH_2$), 30.2 ($CH_2$), 29.9 ($CH_2$), 25.7 ($CH_2$), 23.3 ($CH_2$), 14.3 ($CH_3$); UV-VIS ($CH_3CN$): $\lambda_{max}$ [nm] 459 (MLCT), 255, 261(LIG); Emission: $\lambda_{max}$ [nm] 470; Anal. for $C_{52}H_{76}N_4O_{16}Re_4$, Found (calcd): C, 35.97 (35.53); H, 4.30 (4.36); N, 3.08 (3.18); Mass (FAB, $^{187}$Re): m/z=1760 (M$^+$).

[{$(CO)_3Re(\mu$-$OC_4H_9)_2Re(CO)_3$}$_2(\mu$-bpe)$_2$] (Compound 6): Yield: 76%. IR ($CH_2Cl_2$): $\nu_{CO}$ 2020 (s), 2008 (m), 1909 (m), 1888 (vs) cm$^{-1}$; $^1$H NMR (300 MHz, $(CD_3)_2CO$): $\delta$ 8.46 (d, $^3J$=5.3 Hz, 8H, H$^3$), 7.63 (s, 4H, vinyl), 7.59 (d, $^3J$=5.3 Hz, 8H, H$^2$), 4.41 (m, 8H), 2.13 (m, 8H), 1.49 (m, 8H), 1.08 (t, $^3J$=7.4 Hz, 12H); $^{13}$C NMR (125 MHz; $(CD_3)_2CO$): $\delta$=198.9, 198.5 (1:2, CO), 152.8 (C$^3$), 146.4 (C$^1$), 132.6 (vinyl), 124.0 (C$^2$), 82.5 ($CH_2$), 36.5 ($CH_2$), 19.1 ($CH_2$), 14.5 ($CH_3$); UV-VIS ($CH_3CN$): $\lambda_{max}$ [nm] 398 (MLCT), 289 (LIG); Emission: $\lambda_{max}$ [nm] 440, 454; Anal. for $C_{52}H_{56}N_4O_{16}Re_4$, Found (calcd): C, 35.98 (35.94); H, 3.27 (3.25); N, 3.33 (3.22); Mass (FAB, $^{187}$Re): m/z=1740 (M$^+$).

[{$(CO)_3Re(\mu$-$OC_8H_{17})_2Re(CO)_3$}$_2(\mu$-bpe)$_2$] (Compound 7): Yield: 82%. IR ($CH_2Cl_2$): $\nu_{CO}$ 2020 (s), 2008 (m), 1909 (m), 1886 (vs) cm$^{-1}$; $^1$H NMR (300 MHz, $(CD_3)_2CO$): $\delta$ 8.46 (d, $^3J$=6.6 Hz, 8H, H$^3$), 7.62 (s, 4H, (vinyl)), 7.57 (d, $^3J$=6.6 Hz, 8H, H$^2$), 4.39 (m, 8H), 2.16 (m, 8H), 1.47 (m, 24H), 1.36 (m, 16H), 0.92 (t, $^3J$=6.8 Hz, 12H); $^{13}$C NMR(75 MHz; $(CD_3)_2CO$): $\delta$ 1199.0, 198.6 (1:2, CO), 152.1 (C$^3$), 146.4 (C$^1$), 132.7 (vinyl), 124.1 (C$^3$), 82.8 ($CH_2$), 34.4 ($CH_2$), 32.6 ($CH_2$), 30.4 ($CH_2$), 30.0 ($CH_2$), 26.0 ($CH_2$), 23.3 ($CH_2$), 14.4 ($CH_3$); UV-VIS ($CH_3CN$): $\lambda_{max}$ [nm] 398 (MLCT), 289 (LIG); Emission: $\lambda_{max}$ [nm] 460; Anal. for $C_{68}H_{88}N_4O_{16}Re_4$, Found (calcd): C, 41.58 (41.62); H, 4.47 (4.52); N, 2.85 (2.86); Mass (FAB, $^{187}$Re): m/z=1964 (M$^+$).

[{$(CO)_3Re(\mu$-$OC_4H_9)_2Re(CO)_3$}$_2(\mu$-bpeb)$_2$] (Compound 8): Yield: 78%. IR ($CH_2Cl_2$): $\nu_{CO}$ 2019 (s), 2005 (m), 1905 (m), 1884 (vs) cm$^{-1}$; $^1$H NMR (300 MHz, $(CD_3)_2CO$): $\delta$ 8.36 (d, $^3J$=6.5 Hz, 8H, (pyridyl) H$^3$), 7.54 (d, $^3J$=16.4 Hz, 4H, (vinyl) H$^2$), 7.47 (d, $^3J$=6.5 Hz, 8H, (pyridyl) H$^2$), 7.38 (s, 8H (phenyl)), 7.18 (d, $^3J$=16.4 Hz, 4H (vinyl) H$^1$), 4.40 (m, 8H), 2.13 (m, 8H), 1.49 (m, 8H), 1.08 (t, $^3J$=7.3 Hz, 12H); UV-VIS ($CH_3CN$): $\lambda_{max}$ [nm] 423 (MLCT), 269, 364 (LIG); Emission: $\lambda_{max}$ [nm] 474; Anal. for $C_{68}H_{68}N_4O_{16}Re_4$, Found (calcd): C, 42.37 (42.05); H, 3.42 (3.53); N, 2.92 (2.88); Mass (FAB, $^{187}$Re): m/z=1944 (M$^+$).

[{$(CO)_3Re(\mu$-$OC_8H_{17})_2Re(CO)_3$}$_2(\mu$-bpeb)$_2$] (Compound 9): Yield: 84%. IR ($CH_2Cl_2$): $\nu_{CO}$ 2020 (s), 2006 (m), 1906 (m), 1883 (vs) cm$^{-1}$; $^1$H NMR (300 MHz, $(CD_3)_2CO$): $\delta$ 8.36 (d, $^3J$=6.6 Hz, 8H, (pyridyl) H$^3$), 7.53 (d, $^3J$=16.4 Hz, 4H, (vinyl) H$^2$), 7.46 (d, $^3J$=6.6 Hz, 8H, (pyridyl) H$^2$), 7.38 (s, 8H, (phenyl)), 7.18 (d, $^3J$=16.4 Hz, 4H, (vinyl) H$^1$), 4.39 (m, 8H), 2.15 (m, 8H), 1.47 (m, 24H), 1.37 (m, 16H), 0.92 (t, $^3J$=6.8 Hz, 12H); $^{13}$C NMR(75 MHz; $(CD_3)_2CO$): $\delta$ 199.1, 198.7 (1:2, CO), 152.4 (pyridyl) C$^3$, 148.0 (pyridyl) C$^1$, 137.3 (phenyl) C$^1$, 136.0 (vinyl) C$^2$, 128.5 (phenyl) C$^2$, 125.9 (vinyl) C$^1$, 123.2 (pyridyl) C$^2$, 82.8 ($CH_2$), 34.4 ($CH_2$), 32.6 ($CH_2$), 26.0 ($CH_2$), 23.3 ($CH_2$), 14.4 ($CH_3$); UV-VIS ($CH_3CN$): $\lambda_{max}$ [nm] 422 (MLCT), 235, 285, 370 (LIG); Emission: $\lambda_{max}$ [nm] 474, 490; Anal. for $C_{84}H_{100}N_4O_{16}Re_4$, Found (calcd): C, 46.07 (46.57); H, 4.42 (4.65); N, 1.89 (2.59); Mass (FAB, $^{187}$Re): m/z=2168 (M$^+$).

Crystallographic data: [$C_{68}H_{68}N_4O_{16}Re_4$] (Compound 8): M=1942.06, T=150(1) K, monoclinic, Space group=P2$_1$/n, a=9.2304(1), b=23.5898(1), c=15.9339(2) Å, $\beta$=98.796(1)°, V=3428.69(6) Å$^3$, Z=2, D$_c$=1.881 g/cm$^3$, $\mu$=7.106 mm$^{-1}$, 24951 reflections collected, 7796 independent reflections (R$_{int}$=0.0420), refinement method: full-matrix least-squares on F$^2$, Final R indices [I>2$\sigma$(I)]: R$_1$=0.0379, wR$_2$=0.0658, R indices (all data): R$_1$=0.0512, wR$_2$=0.0699, Largest diff. Peak and hole: 1.187 and −0.786 e Å$^{-3}$. X-ray quality crystals were obtained by solvothermal means and the X-ray diffraction study was carried out for Compound 8. The ORTEP diagram of Compound 8 revealed a rectangular architecture, where two planar bpeb ligands coordinated to four rhenium atoms, which were connected by four butoxy bridges thereby forming a molecular rectangle. Each rhenium atom occupied the corner of the rectangle and was bonded to one nitrogen atom of the pyridyl group of the bpeb ligand, two butoxy groups and three carbonyl groups. In each bridging ligands (bpeb), the two pyridyl groups and the central aromatic ring were oriented in the same plane.

The IR spectra of Compounds 4–9 showed a gradual shift in the carbonyl stretching frequencies, when the ligand was changed from bpeb (bpe) to pz. See, e.g., El-Sayed & Kaesz (1963) Inorg. Chem. 2: 158; and Jiang et al. (1998) Organometallics 17: 173. This indicated that among the three ligands used, the coordinating ability of bpeb and bpe was comparable but stronger than pz. The electronic absorption spectral studies of Compounds 4–9 revealed the existence of two types of bands, one in the UV and the other in the visible region. In a broad way, the higher energy features were assigned to the ligand ($\pi$–$\pi$*) based transition, and the lower energy absorption was assigned to the metal-to-ligand (bridging) charge transfer (MLCT) transition. See, e.g., Giordano & Wrighton (1979) J. Am. Chem. Soc. 101: 2888; Kalyanasundaram Photochemistry of polypyridine and porphyrin complexes, Academic Press, London, 1992; and Meyer (1986) Pure Appl. Chem. 58: 1193. The higher energy absorption ($\pi$–$\pi$*) was always intense, about four fold stronger than the MLCT transition. A red shift of 61 nm (from 398 nm to 459 nm) was felt with the MLCT absorption maxima of these compounds, on changing the ligand from bpe to pz. The observation that the more easily reducible ligands yielded complexes exhibiting lower energy absorption, was in agreement with the results of Wrighton et al. (supra). With the molecular squares, a change of ligand from bpe to pz shifted the lower energy $\lambda_{max}$ from 358 nm to 396 nm (Slone et al. (1996) Inorg. Chem. 35: 4096). Thus the alkoxy bridges facilitate the Re→L charge transfer. It is interesting to note that the (MLCT) band of Compounds 4 and 5 was highly sensitive to the change in the polarity of the solvent and exhibited solvatochromism having a shift in the $\lambda_{max}$ to the tune of 100 nm when the solvent was varied from DMSO to $CCl_4$. Excitation of the complexes near MLCT absorption resulted in moderate emission in the range 440 to 490 nm in $CH_3CN$ and $CH_2Cl_2$. However, the free ligands also showed emission in the above region. Since both the free ligands and rectangles exhibited emissions around the same region, the observed emission for the complexes may therefore be originated from the MLCT band involving primarily the bridging ligands. The excited state lifetimes of these rectangles have been measured and are in the range of 10 to 15 ns at room temperature.

The measured cyclic voltammetric data showed that each of the complexes studied here displays two or three reduction waves and one to four oxidation waves. The first reduction wave in the range −0.73 to −1.28 V can be assigned to the first reduction of the bridging ligand, $L/L^-$. See, e.g., Worl et al. (1991) *J. Chem. Soc., Dalton Trans.* 849; Lin et al. (1992) *Inorg. Chem.* 31: 4346; Stor et al. (1995) *Organometallics* 14: 1115; and Moya et al. (1994) *Inorg. Chem.* 33:2341. The second reduction observed with the complexes containing bpe and bpeb at −1.26 V and −1.28 V may be assigned to the second reduction of the ligand, $L/L^{2-}$. The reduction wave observed in the range of −1.35 to −1.50 V in the case of complexes containing bpe and pz can be assigned to the reduction of metal, $Re^+/Re^0$ (See Lin, supra; and Moya supra). The oxidation peaks observed in the range 1.00–1.65 V may be attributed to the oxidation of four metal centers present in the rectangle. As the alkoxy bridge remains as a good electron donor in the present system it is not able to show any redox reaction in the potential range −2.00 to 2.00 V.

EXAMPLE 3

Synthesis Characterization of Compounds 10–12 Having Rectangular Structures

In a typical preparation, a suspension containing a mixture of $Re_2(CO)_{10}$ (0.199 mmol, 130 mg) and the 4,4′-bipyridine (0.205 mmol, 32 mg) in 10 mL aliphatic alcohol in a 30 mL Teflon flask was placed in an oven maintained at 160° C. and then cooled to 25° C. The crystals were separated by filtration and the solvent from the filtrate was removed by vacuum and the residue was redissolved in minimum quantity of $CH_2Cl_2$ and passed through a short silica gel column to get the pure product. Yield: Compound 10, 84%; Compound 11, 86%; Compound 12, 87%.

Compound 10: IR ($CH_2Cl_2$): $\nu_{CO}$ 2022 (s), 2010 (m), 1912 (m), 1890 (vs) $cm^{-1}$; $^1H$ NMR (300 MHz, $(CD_3)_2CO$): δ 8.65 (d, $^3J=6.6$ Hz, 8H, $H^3$), 7.84 (d, $^3J=6.6$ Hz, 8H, $H^2$), 4.45 (m, 8H), 2.17 (m, 8H), 1.51 (m, 8H), 1.10 (t, $^3J=7.4$ Hz, 12H); $^{13}C$ NMR (75 MHz, $(CD_3)_2CO$): δ 198.9, 198.4 (1:2, CO), 153.6 ($C^3$), 146.2 ($C^1$), 124.2 ($C^2$), 82.7 ($CH_2$), 36.7 ($CH_2$), 19.2 ($CH_2$), 14.6 ($CH_3$); UV-VIS ($CH_3CN$): $\lambda_{max}$ [nm] 384 (MLCT), 249 (LIG); Emission: $\lambda_{max}$ [nm] 666; Anal. for $C_{48}H_{52}N_4O_{16}Re_4$, Found (calcd): C, 34.20 (34.20); H, 3.02 (3.11); N, 3.36 (3.32); Mass (FAB, $^{187}Re$): m/z=1688 ($M^+$).

Compound 11: IR ($CH_2Cl_2$): $\nu_{CO}$ 2022 (s), 2009 (m), 1912 (m), 1890 (vs) $cm^{-1}$; $^1H$ NMR (300 MHz, $(CD_3)_2$ CO)): δ 8.65 (d, $^3J=6.7$ Hz, 8H, $H^3$), 7.83(d, $^3J=6.7$ Hz, 8H, $H^2$), 4.44 (m, 8H), 2.20 (m, 8H), 1.49 (m, 24H), 1.35 (m, 16H), 0.92 (t, $^3J=6.9$ Hz, 12H); $^{13}C$ NMR (75 MHz; $(CD_3)_2CO$): δ=198.8, 198.3 (1:2, CO), 153.5 ($C^3$), 146.1 ($C^1$), 124.1($C^2$), 82.8 ($CH_2$), 34.4 ($CH_2$), 32.5 (2$CH_2$), 30.3 ($CH_2$), 25.8 ($CH_2$), 23.3 ($CH_2$), 14.5 ($CH_3$); UV-VIS ($CH_3CN$): $\lambda_{max}$ [nm] 398 (MLCT), 248 (LIG); Emission: $\lambda_{max}$ [nm] 666; Anal. for $C_{64}H_{84}N_4O_{16}Re_4$, Found (calcd): C, 41.12 (40.24); H, 4.75 (4.43); N, 2.65 (2.93); Mass (FAB, $^{187}Re$): m/z=1912 ($M^+$).

Compound 12: IR ($CH_2Cl_2$): $\nu_{CO}$ 2022 (s), 2010 (m), 1912 (m), 1890 (vs) $cm^{-1}$; $^1H$ NMR (300 MHz, $(CD_3)_2CO$): δ 8.63 (d, $^3J=6.5$ Hz, 8H, $H^3$), 7.80 (d, $^3J=6.5$ Hz, 8H, $H^2$), 4.43 (m, 8H), 2.19 (m, 8H), 1.48 (m, 24H), 1.30 (m, 48H), 0.89 (t, $^3J=6.5$ Hz, 12H); $^{13}C$ NMR (75 MHz; $(CD_3)_2CO$): δ=199.0, 198.3 (1:2, CO), 153.5 ($C^3$), 146.0 ($C^1$), 124.0 ($C^3$), 82.9 ($CH_2$), 34.3 ($CH_2$), 32.6 ($CH_2$), 30.3 (3$CH_2$); 30.0 (2$CH_2$); 25.8 (2$CH_2$); 23.3 ($CH_2$); 14.4 ($CH_3$); UV-VIS ($CH_3CN$): $\lambda_{max}$ [nm] 382 (MLCT), 247 (LIG); Emission: $\lambda_{max}$ [nm] 666; Anal. for $C_{80}H_{116}N_4O_{16}Re_4$, Found (calcd): C, 46.62 (45.01); H, 5.96 (5.48); N, 2.26 (2.62); Mass (FAB, $^{187}Re$): m/z=2136 ($M^+$).

Crystallographic data: [$C_{48}H_{52}N_4O_{16}Re_4$] Compound 10: M=1685.74, T=295(2) K, monoclinic, Space group=$P2_1/n$, a=9.280(2), b=18.613(2), c=15.189(2) Å, β=93.90(2)°, V=2617.6(7) Å$^3$, Z=2, $D_c$=2.139 Mg/m$^3$, µ=9.290 mm$^{-1}$, 4602 reflections collected, 4602 independent reflections, refinement method: full-matrix least-squares on $F^2$, Final R indices [I>2σ(I)]: $R_1$=0.0319, $wR_2$=0.0743, R indices (all data): $R_1$=0.0639, $wR_2$=0.0814, Largest diff. Peak and hole: 1.070 and −1.047 e Å$^{-3}$.

The ORTEP diagram of Compound 10 revealed a rectangular architecture, where two planar bpy ligands coordinated to four rhenium atoms, which were connected by four butoxy bridges thereby forming a molecular rectangle. Each rhenium atom occupied the corner of the rectangle and was bonded to one nitrogen atom of the pyridyl group of the bpy ligand, two butoxy groups and three carbonyl groups. The four butoxy groups were oriented in such a way that they were away from plane bisecting the four Re atoms and two bipyridine ligands. The IR spectra of Compounds 10–12 showed an identical CO stretching pattern similar to the previous reports. The $^1H$ and $^{13}C$ NMR spectral studies and the FAB-MS data of Compounds 10–12 were in agreement with the proposed structures.

The cyclic voltammetric data showed that the Compound 12 displayed two reduction waves and four oxidation waves. The first reduction wave at −1.28 V can be assigned to the reduction of the bridging ligand, (bpy)/(bpy)$^-$ and the second one at −1.50 V to the reduction of metal, $Re^+/Re^0$. The oxidation peaks observed in the range 1.00–1.65 V may be attributed to the oxidation of four metal centers present in the rectangle. The absorption spectrum of Compound 12 showed two peaks in $CH_3CN$ at 250 and 380 nm and they corresponded to the ligand centered (LC) and metal-to-ligand charge transfer (MLCT) transitions, respectively. Addition of water blue shifts the $\lambda_{max}$ of MLCT to 370 nm and increased the absorption intensity. The blue shift in $\lambda_{max}$ was in accordance with negative solvatochromism and the increase in the intensity indicated aggregation of Compound 12.

EXAMPLE 4

Luminescence Enhancement via Aggregation in Compounds 10–12

The molecular rectangles Compounds 10–12 contain long alkyl chains. Surfactants carrying long alkyl chains undergo self-aggregation in aqueous medium and if such aggregation takes place in the presence of metal ions, the term metallo-aggregates is used. See, e.g., Tonellato (1998) *Pure & Appl. Chem.* 70: 1961; and Hamilton Ed. *Perspectives in Supramolecular Chemistry: Supramolecular control of*

Structure and Reactivity; John Wiley & Sons, New York, 1996. A substantial blue shift in the wavelength of emission maximum ($\lambda_{max}^{em}$) from 666 to 602 nm and large enhancement in the emission intensity (a 80-fold increased i.e., from Compound 12 in $CH_3CN$ to 227 in 90% $H_2O$-10% $CH_3CN$) and lifetime has been observed on addition of water to Compound 12 in $CH_3CN$ (Table 1) (The concentration of Compound 12 is 1 $\mu M$). A similar increase in emission quantum yield was also obtained and the values in $CH_3CN$ and in 90% $H_2O$-10% $CH_3CN$ are $0.77\times10^{-4}$ and $16.3\times10^{-4}$, respectively. The change of emission intensity with the change of solvent composition was determined and the lifetime and $\lambda_{max}^{em}$ data was collected as shown in Table 1. The enhancement in emission was marginal with rectangles containing butyl and octyl groups but substantial with dodecyl-containing compounds. The observed blue shift in $\lambda_{max}^{em}$ may be related to the "luminescence rigidochromic effect" that has been recognized for a number of metal carbonyl complexes exhibiting MLCT emission. See, e.g., Kotch et al. (1993) *Inorg. Chem.* 32: 2570; and Lees (1987) *Chem. Rev.* 87: 711. In order to rationalize the rigidochromic effect it is useful to compare the electronic absorption and emission results. Compared to the emission energies, the absorption maximum showed relatively small dependence upon variation of solvent composition. The different behavior of absorption and emission spectral changes can be understood from the different lifetimes of $^1$MLCT and $^3$MLCT states. The absorption and emission spectral results suggested that the relatively long-lived $^3$MLCT ws most affected by the environment changes as it was more susceptible to alterations in dipolar interactions with the molecules present in the medium. In order to confirm the aggregate formation the concentration was measured dependence of emission intensity. Emission intensity increases with an increase in the concentration of the rectangle reached maximum at $2.0\times10^{-5}$ M and remained constant afterwards. Thus the aggregation process was completed at $2.0\times10^{-5}$ M and this value can be taken as critical micellar concentration (CMC).

It is worthwhile to compare these unexpected observations with the results observed by Demas and co-workers (Reitz et al. (1988) *J. Am. Chem. Soc.* 110: 5051) on monometallic Re(I) carbonyl complexes. These authors discovered the remarkable phenomenon that the electronically passive alkyl chains perturbed the emission of Re(I) complex dramatically. They attributed this perturbation to an intramolecular fold back of the chain onto the bipyridine ligand. This fold back perturbed the solvent environment around the excited portion of the complex and altered the excited-state properties. However in a subsequent report (Sacksteder et al. (1993) *J. Am. Chem. Soc.* 115: 8230), they have concluded that the emission enhancement was due to isonitrile impurities. If the intramolecular fold back of the alkyl chain was the major reason for the luminescence enhancement in the present study, it should be felt even in pure solvents i.e., in $CH_3CN$. But in the case of Compounds 10–12, the emission enhancement was observed only in the presence of water and improved with the increase in the water content of the medium. The possible explanation for this emission enhancement was the self-aggregation of molecules carrying long alkyl chains. It has been well established, even in the case of Re(I) complexes, that the emission enhancement is observed when the system is rigid. Thus the emission enhancement in the aqueous medium is due to the rigidity of the molecule resulting from the self-aggregation of the rectangle. The major reason for the poor emission of some metal complexes is the dominance of nonradiative over radiative deactivation of the molecule in the excited state. See, e.g., Turro *Modern Molecular Photochemistry*; Benjamin/Cummings, 1991; and Chen & Meyer (1998) *Chem. Rev.* 98: 1439. The introduction of rigidity either in the molecule or in the medium suppresses the nonradiative transition resulting in luminescence enhancement. To confirm this, the emission spectra of the rectangle in the presence of anionic and cationic surfactants were recorded. The large emission was observed in the presence of low surfactant concentrations but increase in surfactant concentrations led to decrease in emission intensity. To realize the role of added surfactants here, the absorption spectrum of Compound 12 at different concentration of cetyltrimethylammonium bromide (CTAB) was recorded. It is interesting to note that initial addition of CTAB increased the absorption intensity of Compound 12 but the spectrum became closer to the one observed at pure $CH_3CN$ at high CTAB concentrations. Thus, aggregation was complete even in the absence of surfactants and therefore addition of surfactants disturbed the aggregation due to the competitive hydrophobic interaction of the surfactant with the hydrophobic alkyl group of the rectangle.

In order to realize the molecular recognition capability of this luminescent rectangle as host, the reaction of Compound 12 with methyl viologen ($MV^{2+}$) was studied by luminescence quenching technique. The quenching reaction was efficient and the quenching rate constant, $k_q$, value was $1\times10^9$ $M^{-1}s^{-1}$ (calculated from Stern-Volmer plot), close to diffusion controlled rate in 90% $H_2O$-10% $CH_3CN$(v/v). The addition of 1,4-dicyanobenzene to Compound 12 in 50% $H_2O$-50% $CH_3CN$(v/v) shifted the $\lambda_{max}^{em}$ from 613 to 603 nm and increased the luminescence intensity implying binding. Thus Compounds 10–12 can be used as luminescent hosts in host-guest studies.

EXAMPLE 5

Synthesis and Characterization of Compounds 13–15 Having Tetragonal Prismatic Structures Solvothermal synthesis of tetragonal prismatic cages, $[\{(CO)_3Re(\mu_2\text{-}OR)_2Re(CO)_3\}_4(\mu_4\text{-tpeb})_2]$, (13, R=$C_8H_{17}$; 14, R=$C_{12}H_{25}$; 15, R=$C_7H_7$) was carried out using $Re_2(CO)_{10}$ and the ligand tpeb in the alcohol of interest in the ratio 2:1. Prismatic cages 13–15 are the first example of $M_8L_2L_8$ type supramolecules possessing eight octahedral Re(I) centers and two different kinds of ligands, characterized crystallographically having molecular weight more than 4000 and unique having eighteen aromatic rings.

Compound 13. Anal. Calcd for $C_{156}H_{172}N_8O_{32}Re_8$: C, 45.03; H, 4.17; N, 2.69. Found: C, 45.20; H, 4.66; N, 2.33%.

Compound 14. Calcd for $C_{188}H_{236}N_8O_{32}Re_8$: C, 48.99; H, 5.16; N, 2.43. Found: C, 48.95; H, 5.58; N, 2.02%.

Compound 15. Calcd for $C_{162}H_{108}N_8O_{32}Re_8$: C, 46.68; H, 2.61; N, 2.69. Found: C, 46.52; H, 2.61; N, 2.67%.

Compound 15 has been characterized structurally and spectroscopically. Single crystal X-ray crystallographic study of the dark-red crystal of Compound 15 established the stoichiometry, $C_{148}H_{92}N_8O_{32}Re_8(C_6H_5CH_3)_2$. The ORTEP diagram of Compound 15 is shown below and the core geometry of Compound 15 consists of a heavy atom prism made up of eight Re atoms.

The molecular structure of Compound 15 reveals prismatic cage architecture where two planar tpeb ligands coordinate to eight Re atoms which are themselves connected to eight benzyloxy bridges thereby forming a tetragonal prismatic cage. Each Re is bonded to one tpeb nitrogen, two benzyloxy oxygens and three terminal carbonyls. Compound 15 is a unique octanuclear rectangular prismatic cage and the lateral dimension is ~20 (Re1–Re3A)×10 (Re1–Re4)×4 (Re1–Re2) Å. It can also be viewed as a tetragonal prism. Each corner of the rectangular prismatic cage is occupied by $\{(CO)_3Re(\mu_2\text{-}OCH_2C_6H_5)_2Re(CO)_3\}$ moiety where the Re1 and Re2 look like the head and tail of a flying eagle with two benzyloxy wings. Compound 15 consists of eighteen aromatic rings where ten aromatic rings of the two tpeb moieties are oriented in the plane of the molecule with an effective π—π stacking and the remaining eight aromatic rings of the benzyloxy moieties are almost perpendicular to the molecular plane.

Compounds 13–15 displayed CO stretching frequencies in its infrared spectrum similar to that observed for previously reported compounds (e.g., Manimaran et al. (2001). *Eur. J. Inorg. Chem.* 633). The $^1H$ and $^{13}C$ NMR spectra exhibit signals for the presence of tpeb ligand, alkyloxy, benzyloxy moieties and CO groups. The prismatic cages show a sharp absorption at 317 nm and a shoulder at 365 nm irrespective of the polarity of the medium. The sharp intense absorption at 317 nm may be assigned to the π–π* transition of the highly conjugated bridging ligand tpeb and the shoulder at 365 nm to the MLCT transition Re→tpeb in line with the previous reports (e.g., Chen & Meyer (1998) *J. Chem. Rev.* 98: 1439 and references therein). Since some Re(I) containing rectangles are emissive (see Rajendran et al. (2000) *Inorg. Chem.* 39: 2016), the emission spectrum of Compounds 13–15 in THF, DMF and pyridine were recorded and surprisingly, Compounds 13 and 14 were weakly emissive at room temperature when pyridine was used as solvent. The emission maximum was at 648 nm for Compound 13 and 624 nm for Compound 14 and no emission was observed for Compound 15. However, the emission is improved at 77K and the emission maximum is blue shifted to 628 nm. The bi-layer tetragonal supramolecules separated by ~4 Å was weakly emissive due to the π—π stacking of the acetylene groups. When π-acceptor ligands such as pyridine and methyl phenyl sulphide were added, they interacted with the acetylene groups, extended conjugation and made the supramolecule more emissive. The excited state lifetime of Compound 13 and Compound 14 in pyridine at room temperature were both 10 ns. It is worthwhile to recall that the ligand tpeb itself was highly emissive and the emission maximum is at 770 nm. This on complexation was blue shifted to the tune of 146 nm.

As the supramolecules are emissive, use of this property for molecular recognition was studied. The emission spectrum of Compound 13 in pyridine in the absence and presence of different concentration of 1,4-dicyanobenzene were determined. The increase in the emission intensity of Compounds 13 and 14 with the increase in the concentration of 1,4-dicyanobenzene indicates that binding took place between Compounds 13 and 14 and 1,4-dicyanobenzene. The binding constants calculated are in the range of 120 $M^{-1}$ for Compound 13 and 312 $M^{-1}$ for Compound 14. Similar trend has also been observed when methyl phenyl sulphide was used as a guest but the binding constants were below 4 $M^{-1}$. Since Compounds 13–15 are not emissive in THF and DMF solvents, the quenching of these cages with pyrene as photosensitizer was studied. The absorption spectra of pyrene in the absence and presence of Compounds 13–15 were recorded and interestingly found an increase in the absorbance of pyrene due to complex formation. Using Benesi-Hildebrand method (e.g., Murakami et al. (1988) *J. Chem. Soc. Perkin Trans.* 1, 1289; and Benesi & Hildebrand (1949) *J. Am. Chem. Soc.* 71: 2703), the binding constants were found to be in the range of $2.2\text{–}9.2\times10^4$ $M^{-1}$. The quenching of emission intensity of pyrene with the change of the concentration of Compound 15 was also determined. Using the luminescence quenching data, a Stern-Volmer plot (e.g., Rajendran et al. (1997) *J. Chem. Soc. Faraday Trans.* 93: 3155) was plotted, and the plot was linear at low concentration of Compounds 13–15 giving the quenching rate constant value $2.1\text{–}2.6\times10^{13}$ $M^{31}$ $^1s^{-1}$ and at high concentrations deviation from the linearity has been observed. This study indicates strong interaction between pyrene and prismatic cages 13–15. Further, in order to tune the luminescence property of Compound 13–15, the emission spectra of these prismatic cages in THF-$H_2O$ media were recorded. Interestingly, in 80% and 90% water, the emission emerge at 655 and 664 nm for Compound 13, 645 and 666 nm for Compound 14, and 667 and 664 nm for Compound 15 respectively. As discussed previously, it has been observed the molecular aggregation and emission enhancement of alkoxy-bridged Re(I) based molecular rectangles in the presence of water.

In conclusion, the self-assembly of eighteen components into an tetragonal rectangular prismatic supramolecule bearing octahedral Re centers was accomplished in one pot synthesis. It is the first neutral luminescent Re-based supramolecule that is structurally characterized. The presence of lengthy alkyl increases the solubility of these supramolecules dramatically. The luminescence properties and host-guest interaction studies make these tetragonal prismatic cages interesting species.

TABLE 1

Emission Wavelength, Intensity and Lifetime of Compound 12 in Various $CH_3CN$:$H_2O$ (v/v) Mixtures

| | solvent composition | | | | |
|---|---|---|---|---|---|
| no | % $CH_3CN$ | % $H_2O$ | $\lambda_{max}^{em}$ (nm) | Intensity | τ (ns) |
| 1 | 10 | 90 | 602 | 227 | 212 |
| 2 | 20 | 80 | 604 | 166 | 176 |
| 3 | 30 | 70 | 611 | 136 | 167 |
| 4 | 40 | 60 | 612 | 133 | 140 |
| 5 | 50 | 50 | 613 | 124 | 137 |
| 6 | 60 | 40 | 613 | 74 | 135 |
| 7 | 70 | 30 | 611 | 72 | 124 |
| 8 | 80 | 20 | 612 | 59 | 120 |
| 9 | 90 | 10 | 634 | 12 | 13 |
| 10 | 100 | 00 | 666 | 3 | 11 |

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. A tetragonal prismatic supramolecule having the following structure:

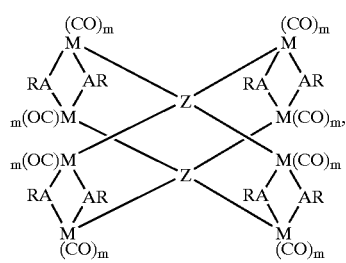

wherein
M is Re, Mn, Cr, Mo, W, Fe, Ru, or Os,
A is O, S, Se, or Te;
R is $C_1$~$C_{16}$ alkyl, $(CH_2)_n$-aryl, or $(CH_2)_n$-aryl-(O-$C_1$~$C_{16}$ alkyl)$_p$, in which n is 0–15, p is 1–3;
m is 1, 2, 3, or 4; and

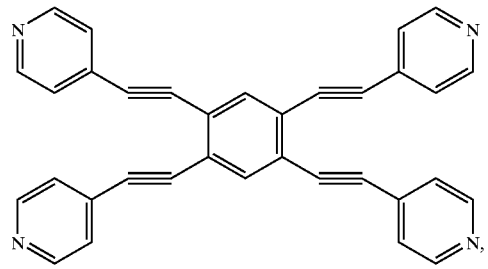

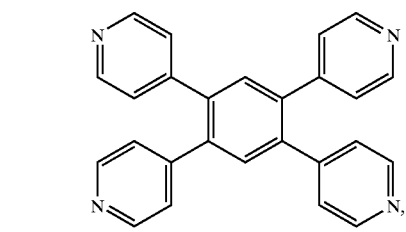

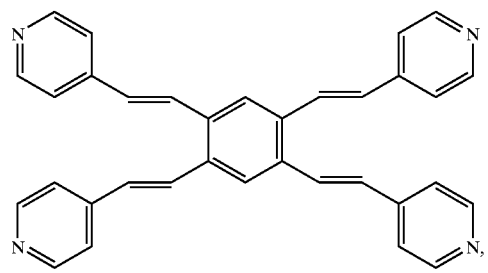

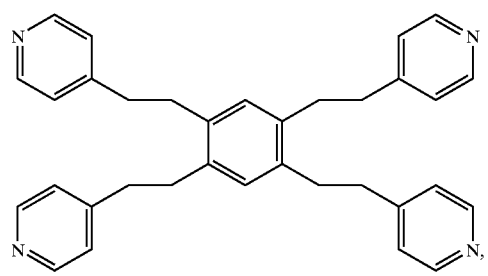

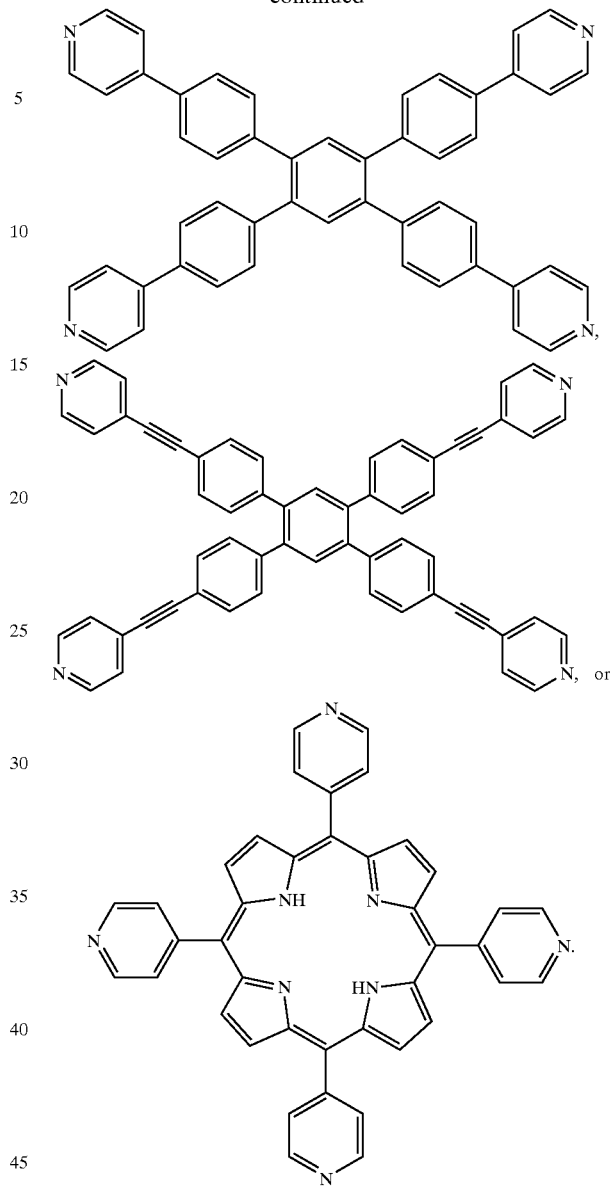

2. The tetragonal prismatic supramolecule of claim 1, wherein M is Re.

3. The tetragonal prismatic supramolecule of claim 2, wherein m is 3.

4. The tetragonal prismatic supramolecule of claim 1, wherein R is $C_1$~$C_{16}$ straight chain alkyl.

5. The tetragonal prismatic supramolecule of claim 1, wherein A is O.

6. A method for making a tetragonal prismatic supramolecule of claim 1, the method comprising reacting $M(CO)_{m+2}$ with a nitrogen-based tetradentate ligand in the presence of an RAH at an elevated temperature to form the prismatic supramolecule, wherein M, m, R, and A are as defined in claim 1.

7. The method of claim 6, wherein M is Re and m is 3.

8. The method of claim 6, wherein RAH is a $C_1$~$C_{16}$ aliphatic alcohol.

9. A composition for emitting luminescence at room temperature, comprising:
 a tetragonal prismatic supramolecule of claim 1 and a solution.

10. The composition of claim 9, wherein M is Re and m is 3.

11. The composition of claim 9, wherein R is a $C_1$~$C_{16}$ aliphatic alkyl.

12. The composition of claim 9, wherein A is O.

13. The composition of claim 9, wherein the solution is an organic or aqueous solution.

14. A hexagonal prismatic supramolecule having the following structure:

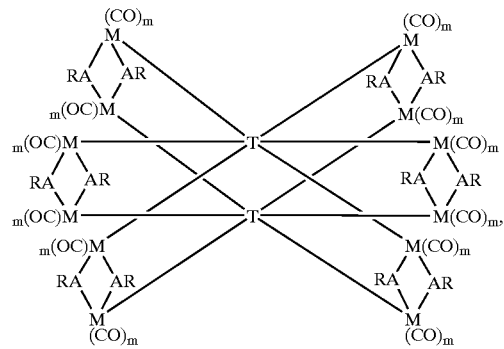

wherein

M is Re, Mn, Cr, Mo, W, Fe, Ru, or Os,

A is O, S, Se, or Te;

R is $C_1$~$C_{16}$ alkyl, $(CH_2)_n$-aryl, or $(CH_2)_n$-aryl-(O-$C_1$~$C_{16}$ alkyl)$_p$, in which n is 0–15, p is 1–3;

m is 1, 2, 3, or 4, and

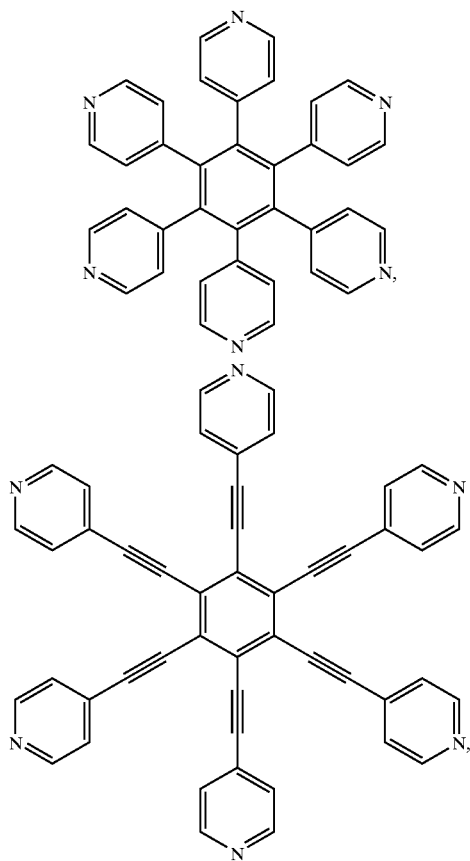

-continued

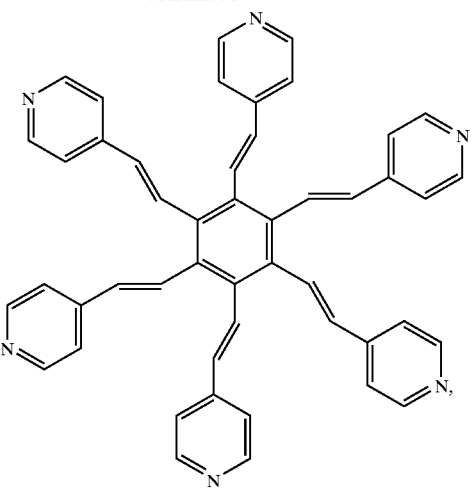

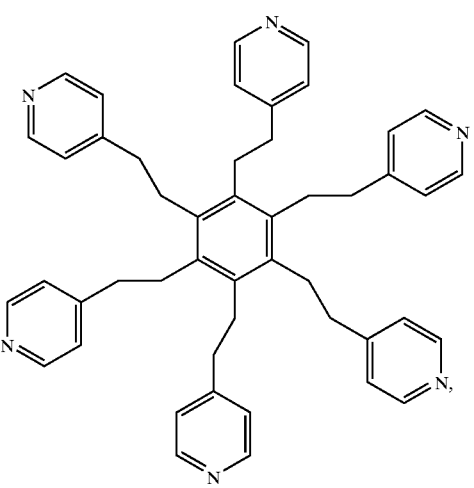

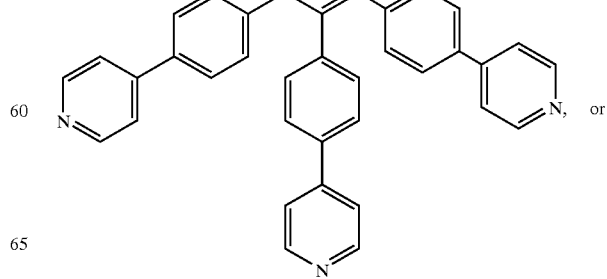

or

-continued

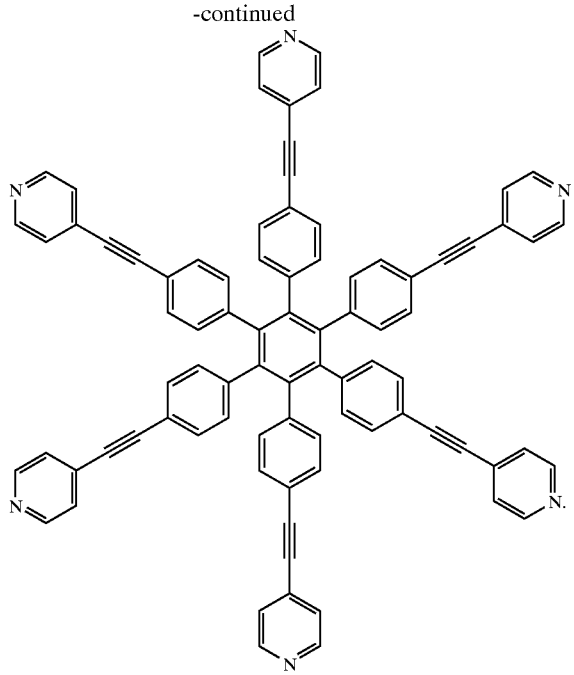

15. The hexagonal prismatic supramolecule of claim 14, wherein M is Re.

16. The hexagonal prismatic supramolecule of claim 15, wherein m is 3.

17. The hexagonal prismatic supramolecule of claim 14, wherein R is $C_1$~$C_{16}$ straight chain alkyl.

18. The hexagonal prismatic supramolecule of claim 14, wherein A is O.

19. A method for making a hexagonal prismatic supramolecule of claim 14, the method comprising reacting $M(CO)_{m+2}$ with a nitrogen-based hexadentate ligand in the presence of an RAH at an elevated temperature to form the hexagonal prismatic supramolecule, wherein M, m, R, and A are as defined in claim 14.

20. The method of claim 19, wherein M is Re and m is 3.

21. The method of claim 19, wherein RAH is a $C_1$~$C_{16}$ aliphatic alcohol.

* * * * *